United States Patent [19]

Jochum et al.

[11] Patent Number: 5,583,164

[45] Date of Patent: Dec. 10, 1996

[54] DENTAL COMPOSITIONS COMPRISING BIFUNCTIONAL OR POLYFUNCTIONAL ACRYLIC-ACID ESTERS OR METHACRYLIC-ACID ESTERS

[75] Inventors: Peter Jochum, Seefeld; Rainer Guggenberger, Hechendorf; Gunther Lechner, Frieding; Klaus Ellrich, Worthsee, all of Germany

[73] Assignee: ESPE Stiftung & Co. Produktions-und Vertriebs KG, Seefeld, Germany

[21] Appl. No.: 451,050

[22] Filed: May 25, 1995

Related U.S. Application Data

[62] Division of Ser. No. 47,381, Apr. 16, 1993, which is a continuation of Ser. No. 452,407, Dec. 19, 1989, abandoned.

[30] Foreign Application Priority Data

Dec. 19, 1988 [DE] Germany .......................... 38 42 681.1

[51] Int. Cl.⁶ ..................... A61F 2/00; C08F 22/26; A61C 5/00
[52] U.S. Cl. ................. 523/115; 526/323.2; 433/228.1; 523/116
[58] Field of Search .................... 523/116, 115; 526/323.2; 433/228.1

[56] References Cited

U.S. PATENT DOCUMENTS

| | | | |
|---|---|---|---|
| 4,221,698 | 9/1980 | Lee, Jr. | 523/115 |
| 4,243,790 | 1/1981 | Foley | 526/323.2 |
| 4,319,015 | 3/1982 | Struver | 526/323.2 |
| 4,552,906 | 11/1985 | Podszûn | 523/115 |
| 4,937,144 | 6/1990 | Podszun | 526/323.2 |
| 4,973,640 | 11/1990 | Matsuda | 526/323.2 |
| 5,021,530 | 6/1991 | Yamamoto | 526/323.2 |

FOREIGN PATENT DOCUMENTS

| | | |
|---|---|---|
| 0211104 | 2/1987 | European Pat. Off. . |
| 0254184 | 7/1987 | European Pat. Off. . |
| 0284991 | 10/1988 | European Pat. Off. . |
| 8101959 | 7/1981 | WIPO . |

*Primary Examiner*—Paul R. Michl
*Assistant Examiner*—LaVonda R. DeWitt
*Attorney, Agent, or Firm*—Birch, Stewart, Kolasch & Birch, LLP

[57] ABSTRACT

Dental compositions based on an at least bifunctional or polyfunctional acrylic-acid and/or methacrylic-acid esters, which contain an initiator system for radical polymerization and which additionally contain a compound of the general formula

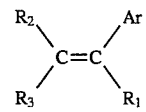

in which:

Ar represents aryl or substituted aryl, $R^1$, $R^2$ and $R^3$ represent hydrogen, aryl or substituted aryl, straight-chain or branched chain $C_{1-18}$-alkyl, $C_{1-18}$-alkoxyl or $C_{1-17}$-alkoxycarbonyl, in which alkyl and alkoxyl can be substituted by halogen or aryl, in which, $R^1$ or $R^2$, when represented by aryl or substituted aryl, $C_{1-18}$-alkyl or $C_{1-18}$-alkoxyl, can be linked with Ar by a single-bond and in which, Ar, when represented by phenyl, $C_{1-18}$-alkylphenyl, $C_{1-18}$-alkoxylphenyl, carboxyl-$C_{1-17}$-alkylphenyl or halogenphenyl, $R^2$ can be represented by —O—, which is linked with the phenyl or phenyl moiety of Ar to a benzofuran, and in which at least one of $R^1$ to $R^3$ represents H, and at least one of $R^1$ to $R^3$ represents aryl or aryl substituted by a straight-chain or branched-chain $C_{1-18}$-alkyl, $C_{1-18}$-alkoxyl, carboxyl-$C_{1-17}$-alkyl or halogen.

As a result of the content of a compound (I) the setting phase of the dental compositions is lengthened.

8 Claims, No Drawings

DENTAL COMPOSITIONS COMPRISING BIFUNCTIONAL OR POLYFUNCTIONAL ACRYLIC-ACID ESTERS OR METHACRYLIC-ACID ESTERS

This application is a divisional of application Ser. No. 08/047,381, filed on Apr. 16, 1993, which is a 37 CFR §1.62 continuation of Ser. No. 07/452,407, filed on Dec. 19, 1989 (now abandoned), the entire contents of which are hereby incorporated by reference.

BACKGROUND AND FIELD OF THE INVENTION

The invention relates to a dental composition comprising (a) 10–99.999% by weight of a functional acrylic-acid and/or methacrylic-acid ester dental compound, (b) 0.001 to 5% by weight of an initiator system capable of initiating radical polymerization, and (c) 0 to 89.999% by weight of auxiliary agents, such as fillers, thixotropic agents and the like, wherein the % by weight is based on the total weight of (a)+(b)+(c).

Dental compositions containing polymerizable dental compounds, e.g. tooth-filling materials, temporary crown and bridge materials or cementing materials, consist of plastics which are provided with organic or inorganic fillers. Depending on the intended application these can be highly liquid to highly viscous compositions. Temporary crown and bridge materials, for example, must on one hand show a good rheology so that they flow throughout the mold in question, on the other hand they must not be so fluid that they would flow out of the mold during a fitting in the jaw. These temporary crown and bridge materials are usually systems having a relatively low amount of fillers, which contain approximately 10 to 70% by weight of inorganic filler. The fillers used generally have an average particle size of 1 to 15 µm. In addition, considerably finer fillers having a particle size of from 0.02 to 0.05 µm are also used with the above fillers to make the compounds sufficiently plastic and thixotropic. The use of organic fillers, such as polymethacrylate, has also proved useful as temporary crown and bridge materials.

When producing such dental composition the object in the past has always been to not only allow the dentist sufficient time for processing, but also to keep the setting phase (that is the amount of time from the start of gelation to the time at which the hardening of the composition is complete), as short as possible, thus keeping the time in which a patient is being treated to a minimum. To achieve this objective, it was necessary to use systems which were as reactive as possible, such systems as photoinitiators or redox catalysts, which initiate the radical polymerization of acrylic-acid and methacrylic-acid esters in a short period of time. For example, European Patent Application 0 059 451 describes the use of certain malonyl sulphamides as activators for the peroxidic polymerization of polymerizable dental compounds. One of the advantages mentioned therein is the short setting phase despite the long processing time. In a similar manner the German laid open print 14 95 520 describes a process for the polymerization of acrylic-acid esters in which a catalyst system, consisting of organic peroxide, ionogenic halogen, a copper compound and a barbituric acid is used as the activator.

Even when photoinitiators were used the object was to employ the most reactive possible systems for the polymerizable dental compounds. This made possible a rapid polymerization in the short irradiation phase. For example, European Patent Specification 1 84 095 describes particularly reactive bis-acylphosphine oxides as photoinitiators for dental compounds.

The use of the most reactive possible initiator systems for the polymerization of the dental compounds based on acrylic-acid or methacrylic-acid esters has admittedly brought the advantage that hard plastic materials can be obtained in very short periods of time, for the dentist. However, because of the extremely rapid setting phase the problem arose that for some applications the time for preparing and processing the dental materials was too short, particularly for removing temporary crown and bridge materials.

Adhesive compositions are known from European Patent Application 211 104 which contain vinyl compounds and a compound of the general formula

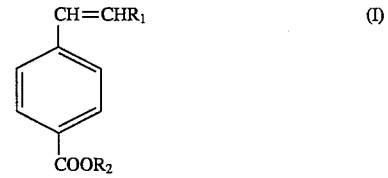

in which $R_1$ represents hydrogen or methyl and $R_2$ represents hydrogen or an optionally substituted alkyl radical with 1 to 5 carbon atoms. Bifunctional methacrylic-acid esters are mentioned among others as the vinyl compounds. Moreover, hardened resins and their use for the production of optical lenses are known from the German laid open print 31 20 965, which have been manufactured from bifunctional acrylic-acid or methacrylic-acid esters and a further unsaturated compound, in which the further unsaturated compound can be styrene, alpha-$(C_{1-3})$-alkylstyrene, vinyl naphthalene, etc. Tests have however shown that unsaturated compounds with only one aromatic radical such as described in the two above publications do not have a satisfactory effect with regard to the lengthening of the setting phase. Such additives are in any case only effective in very high concentrations and even then not to a satisfactory degree. It could therefore be established that the alpha-methylstyrene mentioned by way of example in the above published application is unable to effect any useful lengthening of the setting phase. Moreover, this type of compound has problems with regard to storage-stability and processing due to its low volatility, and in many areas of application, e.g., in dental compositions, the addition of readily volatile compounds is undesirable.

SUMMARY OF THE INVENTION

The object of the invention is therefore to prepare dental compositions comprising polymerizable dental compounds, particularly temporary crown and bridge materials, with an extended setting phase so that these materials can be processed over a longer period, and still result in having the excellent end-hardness of a polymerized dental material.

The present invention further relates to a dental composition comprising (a) 10–99.999% by weight of at least a bifunctional, or polyfunctional, e.g., trifunctional, acrylic-acid and/or methacrylic-acid ester dental compound, (b) 0.001 to 5% by weight of an initiator system capable of initiating radical polymerization, and (c) 0 to 89.999% by weight of auxiliary agents, such as fillers, thixotropic agents and the like, wherein the % by weight is based on the total weight of (a)+(b)+(c), and (d) 0.001 to 10% by weight, based on the weight % of (a), of a dental compound of the general formula

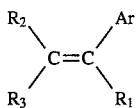

in which:

Ar represents aryl or substituted aryl, which is substituted by straight-chain or branched-chain $C_{1-18}$alkyl, $C_{1-18}$-alkoxyl, carboxyl-$C_{1-17}$-alkyl or halogen, $R^1$, $R^2$ and $R^3$, which are the same or different, represent hydrogen, aryl or substituted aryl, which is substituted by straight-chain or branched-chain $C_{1-18}$-alkyl, $C_{1-18}$-alkoxyl, carboxyl-$C_{1-17}$-alkyl or halogen, or represent a straight-chain or branched-chain $C_{1-18}$-alkyl, $C_{1-18}$-alkoxyl, or $C_{1-17}$-alkoxycarbonyl, in which alkyl and alkoxyl can be substituted by halogen or aryl, in which, $R^1$ or $R^2$, when represented by aryl or substituted aryl, which is substituted by straight-chain or branched-chain $C_{1-18}$-alkyl, $C_{1-18}$-alkoxyl, carboxyl-$C_{1-17}$-alkyl or halogen, or when represented by $C_{1-18}$-alkyl or $C_{1-18}$-alkoxyl, can be linked with Ar by a single bond and in which, Ar, when represented by phenyl, $C_{1-18}$-alkylphenyl, $C_{1-18}$ alkoxyphenyl, carboxyl-$C_{1-17}$-alkylphenyl or halophenyl, $R^2$ can be represented by —O—, which is linked with the phenyl or phenyl moiety of Ar to a benzofuran and in which, at least one of $R^1$ to $R^2$ represents H and at least one of $R^1$ to $R^2$ represents aryl or aryl substituted by straight-chain or branched-chain $C_{1-18}$-alkyl, $C_{1-18}$-alkoxyl, carboxyl-$C_{1-17}$-alkyl or halogen.

Preferred dental compositions are compositions in which, Ar of dental compound (d) of general formula I represents phenyl, naphthyl or anthryl, which can be substituted by $C_{1-18}$-alkyl, $C_{1-18}$-alkoxyl, carboxyl-$C_{1-17}$-alkyl or halogen.

Preferably two of $R^1$ to $R^3$ of formula I represent H, and of these two are preferably $R^2$ and $R^3$. Further preferred is a compound of general formula I in which $R^1$ and Ar are the same and represent phenyl, $C_1$–$C_6$-alkylphenyl, $C_1$–$C_6$-alkoxylphenyl or carboxyl-$c_{1-6}$-alkylphenyl. A compound of general formula I is also preferred in which $R^1$ has the meaning of Ar, but $R^1$ and Ar are different from each other.

The dental composition preferably comprises dental compound (d) in a quantity of 0.01 to 5% by weight, and particularly preferred in a quantity of 0.05 to 2% by weight, based on the weight % of dental compound (a).

A large number of the compounds of general formula I are commercially available and/or their production process is known. For example, 1,1-diphenylethylene can be produced by the reaction of phenylmagnesium-bromide with acetic-acid ester and subsequent elimination of water, see e.g. Organic Synthesis Coll. Vol. I, page 226 ff. (1948, 2nd edition).

Compounds of formula I in which $R^2$ and $R^3$ are H, can also be obtained in the known manner from the corresponding carbonyl compounds by means of the so-called Wittig Synthesis, see e.g. Macro Molecules 9, 716 (1976).

The invention also relates to the use of a compound of the general formula I in the production of dental compositions which contain at least bifunctional acrylic-acid and/or methacrylic-acid esters.

The at least bifunctional acrylic-acid and/or methacrylic-acid esters to be used as the component (a) dental compounds according to the invention can include monomeric and polymeric acrylates and methacrylates. These compounds utilized as component (a) are preferably bifunctional, but they can also be polyfunctional; e.g. trifunctional. The compounds, however, should at least be bifunctional. Thus, as used herein, the term "an at least bifunctional" is intended to mean bifunctional and polyfunctional and, therefore, encompass compounds which are bifunctional, trifunctional, etc. Advantageously used are, for example, the long-chain monomers of U.S. Pat. No. 3,066,112 based on bisphenol A and glycidyl methacrylate or derivatives thereof formed by the addition of isocyanates. Compounds of the type bisphenol-A-diethyloxy(meth)-acrylate and bisphenol-A-dipropyloxy(meth)-acrylate are also suitable. The oligo-ethoxylated and oligo-propoxylated bisphenol-A-diacrylic-acid and -dimethacrylic-acid esters can also be used.

The acrylic-acid and methacrylic-acid esters of bifunctional, or polyfunctional, e.g., trifunctional, aliphatic alcohols are also well suited, for example, triethyleneglycol-di(meth)-acrylate, ethyleneglycol-di(meth)-acrylate, hexanediol-di(meth)-acrylate and trimethylolpropane-tri-(meth)-acrylate.

Particularly suitable are also the diacrylic-acid and dimethacrylic-acid esters of bis(hydroxymethyl)-tricyclo [5.2.1.0$^{2,6}$]-decane mentioned in German Patent Specification 28 16 823, and the diacrylic- and dimethacrylic-acid esters of the compounds of bis-(hydroxylmethyl)-tricyclo [5.2.1.0$^{2,6}$]-decane lengthened with 1 to 3 ethylene oxide and/or propylene oxide units.

Well-suited monomers are also the methacrylic-acid esters described in European Published Specification 0235826, e.g., triglycollic acid-bis[3(4)-methacryloxymethyl-8(9)-tricyclo[5.2.1.0$^{2,6}$]-decylmethylester.

Mixtures of monomers and/or of unsaturated polymers produced therefrom can clearly also be used.

In addition to the bifunctional, or polyfunctional, e.g. trifunctional, acrylic-acid and methacrylic-acid ester, there can be used up to 70% by weight, based on the weight % of (a), preferably up to 50% by weight of a monofunctional methacrylic-acid ester, such as methylmethacrylate.

As constituent (b), the initiator system is one which is capable of initiating the radical polymerization of at least a bifunctional, or polyfunctional, e.g. trifunctional, monomer, e.g., a photoinitiator or a so-called redox initiator system.

As the photoinitiators, e.g., alpha-diketones are suitable, such as camphorquinone, in combination with secondary and tertiary amines, or mono- and bisacylphosphinoxides, such as 2,4,6-tri-methylbenzoyl-diphenyl-phosphineoxide and bis(2,6-dichloro-benzoyl)-4-n-propylphenyl-phosphineoxide. Other compounds of this type are, however, also suitable, as photoinitiators, such as those described in the European Patent Specifications 73 413, 7 508, 47 902, 57 474 and 184 095.

The concentration of the photoinitiators is preferably 0.01 to 3% by weight, particularly preferably 0.1 to 2% by weight, based on the total weight of (a)+(b)+(c).

Organic peroxide compounds together with so-called activators are suitable as redox initiator systems. As organic peroxide compounds, in particular, compounds such as laurel peroxide, benzoyl peroxide and also p-chlorobenzoyl peroxide suitable.

Suitable activators are, for example, tertiary aromatic amines, such as N,N-bis-(hydroxyalkyl)-3,5-xylidines known from U.S. Pat. No. 3,541,068 and also the N,N-bis-(hydroxyalkyl)-3,5-di-t-butylanilines known from the German laid open prints 26 58 530, particularly N,N-bis-(beta-oxybutyl)-3,5-di-t-butylaniline.

Well-suited activators are also the barbituric acids and barbituric acid derivatives described in the German published examined application 14 95 520 and also the malonylsulphamides described in the European Patent Specification 0 059 451. Preferred malonylsulphamides are 2,6-dimethyl-4-isobutyl-malonylsulphamide, 2,6-diisobutyl-4-propylmalonylsulphamide, 2,6-dibutyl-4-propylmalonylsulphamide, 2,6-dimethyl-4-ethyl-malonylsulphamide and also 2,6-dioctyl-4-isobutyl-malonylsulphamide.

For further acceleration, the polymerization is carried out preferably in the presence of heavy-metal compounds and ionogenic halogen or pseudo-halogen. Copper is particularly suitable as the heavy metal, and the chloride ion is particularly suitable as the halide. The heavy metal is suitably used in the form of soluble organic compounds. In a similar way the halide and pseudo-halide ions are suitably used in the form of soluble salts, examples that can be mentioned are soluble aminohydrochlorides and also quaternary ammonium chloride compounds.

If component (b) of the dental composition according to the invention comprises a redox initiator system comprised of organic peroxide and activator, then the peroxide and activator are preferably present in the composition in spatially separate parts and are only mixed together homogeneously immediately before use.

If component (b) of the dental composition according to the invention comprises an organic peroxide, copper compound, halide and malonyl sulphamide, then it is particularly useful for the organic peroxide, malonyl sulphamide and the combination of the copper compound/halide to be present in the composition in three spatially separate parts. For example, the organic peroxide, polymerizable monomers and also fillers can be kneaded into a paste and the other components can be kneaded into two other separate pastes, in the manner described above, each comprising a small amount of fillers or particularly thixotropic agents, such as silanized silicic acid, and a plasticizer, for example, a phthalate. On the other hand the polymerizable monomers can also be present together with the copper compound/halide and fillers. If the dental composition according to the invention is in spatially separate parts, component (d) can be present in each of these parts.

In addition to the at least bifunctional, or polyfunctional, e.g. trifunctional, acrylic-acid and methacrylic-acid ester (a) and the initiator system (b), the composition can contain up to 89.999% by weight, based on the total weight of (a)+(b)+(c), of auxiliary agents, such as organic and/or inorganic fillers, pigments, colorants, thixotropic agents, plasticizers and the like.

Inorganic fillers can, for example, be quartz, ground glass, poorly soluble fluorides, such as $CaF_2$, $YF_3$, silica gels and silicic acid, particularly pyrogenic silicic acid or their granulates. They are preferably contained in the dental compositions in a concentration of 2 to 85% by weight, particularly preferred from 30 to 70% by weight, based on the total weight of (a)+(b)+(c). For better incorporation into the polymer matrix it can be of advantage, to render the fillers hydrophobic and, if appropriate, x-ray opaque additives such as yttrium fluoride. The usual hydrophobic inducing agents are silanes, for example, trimethoxymethacryloxypropyl-silane. The maximum average particle size of the inorganic fillers is preferably 15 μm, particularly 10 μm. It is more preferred for fillers with an average particle size of <5 μm to be used.

Already pigmented polymethylmethacrylate beads or other pulverized organic polymerisates are suitable as fillers. To increase the flexibility of the dental compositions it can also be advantageous to use soluble organic polymers. Those suitable are, e.g. polyvinylacetate and copolymers based on vinyl chloride/vinyl acetate, vinyl chloride/vinylisobutylether and vinyl acetate/maleic acid dibutylether. Well-suited as additional plasticizers are, for example, dibutyl-, dioctyl- and dinonyl-phthalates.

The dental compositions according to the invention have the following advantages:

1. With the photopolymerizable dental compositions according to the invention, through the use of component (d), the polymerization to hard polymers are no longer suddenly formed within a few seconds (10–20 seconds), but instead the polymerization proceeds evenly over a period of 20 to 60 seconds and as a result, stresses which could occur inside the polymers can be avoided. If the dental composition according to the invention is exposed to light for only a short period of time (10–30 sec.), the material is still readily workable mechanically and can be further hardened in subsequent stages of light-exposure. With tooth-filling materials, in particular, better results are obtained in tooth-fillings with respect to marginal fissures and adhesion to the surrounding tooth material. The occurrence of micro-cracks from stresses is also reduced and as a result the abrasion resistance of the material is improved. A further advantage is that due to the slow setting only a moderate temperature increase occurs due to the reaction heat liberated during the polymerization.

2. With the redox-polymerized dental compounds of the dental composition according to the invention, in addition to the aforementioned advantages one obtains a good workability of the compounds after the polymerization has begun, i.e. the rubber-elastic transition state is maintained for longer and thus any surplus can still be readily removed during the cementing and positioning of a filling.

3. The dental compositions according to the invention have a particular advantage when used as temporary crown and bridge material. Because of the longer rubber-elastic setting phase it is possible for the dentist to remove the temporary structure from the mouth of the patient when it is not yet in a completely hardened state and to perform work thereon without endangering its dimensional stability. In contrast to previous materials, a period of several minutes is available for the removal of the temporary structure, so that even temperature influences, the size of the temporary structure and the storage of the materials, have little effect on its processibility.

EXAMPLE 1

Polymerizable dental composition 100 g of 2,2-bis{4-[oligo(ethoxy)]-phenyl}-propane-dimethacrylate (Diacryl-121, Akzo Co.), 0.3 g of (beta-phenyl-ethyl)-dibutyl-ammonium-chloride, 60 mg of bis-(1-phenyl-pentane-1,3-dionato)-copper (II) and also the quantities corresponding to the data in Table 1 of the compound (d) used according to the invention, are mixed into a homogeneous solution. The solution thus made is kneaded with 21 g of tooth-colored, silanized, micro-fine silicic acid into a still flowable paste. 75 g of this paste is mixed homogeneously with 3 g of a lauroylperoxide paste (25% in dioctylphthalate) and 3 g of a paste, containing 25% by weight of 2,6-dibutyl-4-isobutylmalonylsulphamide in dioctylphthalate. The setting phases given in the table are determined from this mixture by means of a curometer (Wallace-Shawberry Co.).

TABLE 1

| No. | Compound (d) | Added Amt of (d) in % by wt. based on (a) | Time-Reading for Setting Phase in Curometer at 23° | Setting Phase (min.) |
|---|---|---|---|---|
| 1 | — | 0 | 3'30" to 6'50" | 3'20" |
| 2 | 2,5-dimethylstyrene | 2 | 3'30" to 7'10" | 3'10" |
| 3 | trans-stilben | 2 | 5'30" to 11'10" | 6'00" |
| 4 | 1,2-dihydro-4-phenylnaphthalene | 2 | 3'50" to 9'00" | 5'10" |

EXAMPLE 2

A homogeneous solution is produced from 100 g of Diacryl-121 (see Example 1), 0.3 g N,N-dibutyl-betaphenylethylaminohydrochloride and 0.06 g of compound (d). 21 g of tooth-colored, silanized, micro-fine silicic acid is added and kneaded to a still pourable paste. Then 75 g of this paste is mixed homogeneously with 3 g each of the lauroyl peroxide paste and malonylsulphamide paste described in Example 1 and the setting phase is determined by means of a curometer.

TABLE 2

| No. | Compound (d) | Time-Reading for Setting Phase in Curometer at 23° | Setting Phase (min.) |
|---|---|---|---|
| 5 | — | 1'10" to 3'00" | 1'50" |
| 6 | alpha-methylstyrene | 1'10" to 3'05" | 1'55" |
| 7 | 1,1-diphenylethylene | 2'30" to 13'00 | 10'30" |
| 8 | 1,1-bis(-4-methoxyphenyl)ethylene | 3'40" to 12'00" | 8'20" |
| 9 | 1-(4-methoxyphenyl)-1-phenylethylene | 2'50" to 12'00" | 9'10" |
| 10 | 1-(3,4-dimethylphenyl)-1-phenyl-ethylene | 2'40" to 11'30" | 8'50" |
| 11 | 1-(4-chlorophenyl)-1-phenylethylene | 2'25" to 11'40" | 9'15" |
| 12 | 1-(2,5-dimethylphenyl)-1-phenyl ethylene | 1'40" to 5'30" | 3'50" |

EXAMPLE 3

Example of use—manufacture of a semi-permanent bridge 1.5 g of the activated mixture according to Example 2, No. 7, is introduced with a syringe into an alginate impression, which had been formed from the patient's mouth prior to the preparation of the bridge-supporting teeth and in which a deep groove is cut between the impressions of the supporting teeth. The filled impression is introduced into the mouth of the patient and after the beginning of the setting phase (within 4 to 10 minutes after the start of mixing) and removed from the mouth again with the mould. During the setting phase only a slight increase in temperature occurred. Table 3 shows some physical values. The compressive strength of the hardened material was determined using cylindrical test pieces with a diameter of 4 mm and a height of 8 mm, the bending strength was determined using test pieces with the dimensions 4×4×25 mm.

TABLE 3

| Material | Time Available for Removal | Hardened Material Compressive Strength | Bending Strength |
|---|---|---|---|
| Example 2, No. 7 (acc. to invention) | 5–10 min. after start of mixing | 270 MPa | 90 MPa |
| "Protemp", ESPE Co. (comparison) | 5–6 min. after start of mixing | 180 MPa | 80 MPa |
| Acrylate basis, "Trim", Bosworth Co. (comparison) | 4–8 min. after start of mixing | 70 MPa | 60 MPa |

Result

Compared with the commercially available material based on dimethylacrylic-acid ester (Protemp, ESPE Co.), the material according to the invention has distinctly higher mechanical strengths due to reduced stresses during polymerization and a considerably lengthened removal period which clearly simplifies the processing by the dentist. Compared with classical material based on monofunctional acrylates (Trim, Bosworth Co.), the material according to the invention also has an increased removal period and also has distinctly better mechanical properties.

EXAMPLE 4

Photo-polymerizable solution 98.8% by weight of bis-(acryloyloxymethyl)tricyclo [$5.2.1.0^{2,6}$]-decane, 1% by weight of dimethylethanolamine and 0.2% by weight of camphorquinone are stirred together until a homogenous, clear yellowish solution forms (production of mixture with daylight excluded). The % by weight values of diphenyl-ethylene given in the table are added to the solutions and the solutions are then irradiated with a dental halogen light-device (ELIPAR, ESPE Co., 400 to 500 nm) until the maximum reaction temperature is reached (measured in a cylindrical form, diameter: 3 mm, height: 2 mm).

TABLE 4

| No. | % by weight of diphenylethylene, referred to (a) | maximum temperature (°C.) | time to reach the maximum temperature (sec.) |
|---|---|---|---|
| 13 | 0 | 80 | 18 |
| 14 | 0.03 | 78 | 24 |
| 15 | 0.06 | 74 | 25 |

Result

Compared with a material without the additive used according to the invention, the materials according to the invention show a clearly lengthened setting phase, which in addition leads to lower temperature peaks during the polymerization.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A method of producing a cured dental composition, comprising the steps of:

Step 1) providing a polymerizable dental composition comprising:
(a) 10 to 99.999% by weight of a bifunctional or polyfunctional acrylic-acid and/or methacrylic-acid ester dental compound,
(b) 0.001 to 5% by weight of an initiator system capable of initiating radical polymerization,
(c) 0 to 89.999% by weight of an auxiliary agent that is selected from the group consisting of an organic filler, an inorganic filler, a pigment, a colorant, a thixotropic agent and a plasticizer, wherein the % by weight is based on the total weight of (a)+(b)+(c), and
(d) 0.001 to 2% by weight, based on the weight % of (a), of a dental compound of the general formula:

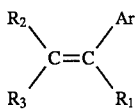
I in which:
Ar and $R_1$, which are the same or different, each represent an aryl or a substituted aryl, which is substituted by a straight-chain or branched-chain $C_{1-18}$-alkyl, $C_{1-18}$-alkoxy, carboxyl-$C_{1-17}$-alkyl or halogen, and $R_1$ may be linked to Ar by a single bond,
$R^2$ and $R^3$, each represent a hydrogen atom; and
Step 2) polymerizing and shaping the dental composition provided, so that said cured dental composition is obtained.

2. The method of claim 1, wherein the cured dental composition is in the form of a dental restorative.

3. The method of claim 1, wherein the cured dental composition is in the form of a temporary dental restorative.

4. The method of claim 1, wherein the cured dental composition is in the form of a dental restorative selected from the group consisting of a dental crown, a dental bridge and a dental filling.

5. The method of claim 1, where in Step 1 of the method, the dental compound (d) of general formula I is present in an amount of 0.05 to 2% by weight, based on the weight % of (a).

6. The method of claim 1, where in Step 1 of the method, Ar of dental compound (d) of general formula I represents phenyl, naphthyl or anthryl, which can be substituted by $C_{1-18}$-alkyl, $C_{1-18}$-alkoxy, carboxyl-$C_{1-17}$-alkyl or halogen.

7. The method of claim 1, where in Step 1 of the method, $R^1$ and Ar of dental compound (d) of general formula I, are the same and represent phenyl, $C_{1-6}$-alkyl-phenyl, $C_{1-6}$-alkoxyphenyl or carboxy-$C_{1-6}$-alkyl-phenyl.

8. The method of claim 1, wherein said component (d) dental compound is present in said polymerizable dental composition in an amount which provides said polymerizable dental composition with a setting time (curing time) that is at least twice that of an identical dental composition not containing said component (d) dental compound.

* * * * *